United States Patent
Zhang et al.

(10) Patent No.: US 10,717,041 B2
(45) Date of Patent: Jul. 21, 2020

(54) CARBON MOLECULAR SIEVE MEMBRANES FOR AGGRESSIVE GAS SEPARATIONS

(71) Applicants: Georgia Tech Research Corporation, Atlanta, GA (US); Shell Oil Company, Houston, TX (US)

(72) Inventors: Chen Zhang, Atlanta, GA (US); William John Koros, Atlanta, GA (US); Joseph Marshall Mayne, Richmond, TX (US); Paul Jason Williams, Richmond, TX (US)

(73) Assignees: SHELL OIL COMPANY, Houston, TX (US); GEORGIA TECH RESEARCH CORPORATION, Atlanta, GA (US)

( * ) Notice: Subject to any disclaimer, the term of this patent is extended or adjusted under 35 U.S.C. 154(b) by 81 days.

(21) Appl. No.: 15/889,670

(22) Filed: Feb. 6, 2018

(65) Prior Publication Data
US 2018/0229181 A1  Aug. 16, 2018

Related U.S. Application Data

(60) Provisional application No. 62/457,253, filed on Feb. 10, 2017.

(51) Int. Cl.
  *B01D 53/22* (2006.01)
  *B01D 71/02* (2006.01)
  (Continued)

(52) U.S. Cl.
  CPC ....... *B01D 53/228* (2013.01); *B01D 67/0067* (2013.01); *B01D 69/02* (2013.01);
  (Continued)

(58) Field of Classification Search
  CPC .. B01D 53/228; B01D 67/0067; B01D 69/02; B01D 69/08; B01D 71/021;
  (Continued)

(56) References Cited

U.S. PATENT DOCUMENTS

| | | | | |
|---|---|---|---|---|
| 6,299,669 B1 * | 10/2001 | Koros | ................. | B01D 53/228 95/51 |
| 2002/0139749 A1 | 10/2002 | Tan et al. | | |

(Continued)

OTHER PUBLICATIONS

Vu, De Q. et al., "High Pressure CO2/CH4 Separation Using Carbon Molecular Sieve Hollow Fiber Membranes", Ind. Eng. Chem. Res., 2002, 41, pp. 367-380. (Year: 2002).*

(Continued)

*Primary Examiner* — Jason M Greene
(74) *Attorney, Agent, or Firm* — McAndrews, Held & Malloy, Ltd.

(57) ABSTRACT

The present disclosure describes a process for separating at least a first gas component and a second gas component by contacting a gas stream comprising the first and second gas components with a carbon molecular sieve (CMS) membrane under aggressive gas separation conditions in which the partial pressure of the selectively sorbed gas component in the gas stream is high. Despite the high partial pressure of the sorbed gas component, the selectivity of the carbon molecular sieve membrane is not substantially reduced by plasticization or saturation. In some embodiments, the aggressive gas separation process may include contacting a gas stream at supercritical conditions with a CMS membrane to separate at least first and second gas components. The process may be useful for, among other things, the separation of $CO_2$ from a natural gas stream.

16 Claims, 6 Drawing Sheets

(51) Int. Cl.
*B01D 69/08* (2006.01)
*B01D 67/00* (2006.01)
*C10L 3/10* (2006.01)
*C07C 7/13* (2006.01)
*C07C 7/144* (2006.01)
*B01D 69/02* (2006.01)

(52) U.S. Cl.
CPC .......... *B01D 69/08* (2013.01); *B01D 71/021* (2013.01); *B01D 71/028* (2013.01); *C07C 7/13* (2013.01); *C07C 7/144* (2013.01); *C10L 3/102* (2013.01); *C10L 3/103* (2013.01); *C10L 3/104* (2013.01); *B01D 2256/10* (2013.01); *B01D 2256/24* (2013.01); *B01D 2256/245* (2013.01); *B01D 2257/304* (2013.01); *B01D 2257/504* (2013.01); *B01D 2257/702* (2013.01); *B01D 2325/02* (2013.01); *C10L 2290/542* (2013.01); *C10L 2290/548* (2013.01); *Y02C 10/04* (2013.01); *Y02P 20/544* (2015.11)

(58) Field of Classification Search
CPC ............ B01D 71/028; B01D 2257/504; B01D 2257/702; B01D 2257/7022; C10L 3/102; C10L 3/103; C10L 3/104
See application file for complete search history.

(56) References Cited

U.S. PATENT DOCUMENTS

| | | | |
|---|---|---|---|
| 2011/0041687 A1* | 2/2011 | Diaz | B01D 53/228 95/49 |
| 2011/0077446 A1* | 3/2011 | Shanbhag | B01D 53/226 585/818 |
| 2013/0333562 A1* | 12/2013 | Koros | B01D 53/228 95/50 |
| 2015/0094445 A1* | 4/2015 | Bhuwania | B01D 53/228 528/210 |
| 2018/0001270 A1* | 1/2018 | Swaidan | B01D 71/021 |

OTHER PUBLICATIONS

Vu et al., High Pressure CO2/CH4 Separation Using Carbon Molecular Sieve Hollow Fiber Membranes, Industrial & Engineering Chemistry Research, vol. 41, No. 3, 2002 [retrieved on Mar. 13, 2018] Retrieved from the Internet: <URL:https://pubs.acs.org/doi/abs/10 1021/ie010119w>. see abstract.

Kosuri, Polymeric Membranes for Super Critical Carbon Dioxide (scCO2) Separations, Georgia Institute of Technology, May 2009 [retrieved on Mar. 13, 2018]. Retrieved from the Internet: <URL: https://smartech.gatech.edu/bitstream/handle/1853/28242/Kosuri_Madhava_R_200905_PhD.pdf.pdf>. pp. 102, 103, 107, 108, 145, 146, 160.

Zhang, et al., Purification of Aggressive Supercritical Natural Gas Using Carbon Molecular Sieve Hollow Fiber Membranes, Industrial & Engineering Chemistry Research, vol. 56, Aug. 25, 2017 [retrieved on Mar. 13, 2018]. Retrieved from the Internet: <URL: https://wqjin-group.com/wp.content/uploads/2012/11/2017-Chen-Zhang-IECR.pdf>. pp. 10482-10490.

International Search Report and Written Opinion for PCT/US2018/017051, dated Apr. 9, 2018, 10 pages.

* cited by examiner

CARBON MOLECULAR SIEVE MEMBRANES FOR AGGRESSIVE GAS SEPARATIONS

This application claims priority to U.S. Provisional Patent Application No. 62/457,253, filed Feb. 10, 2017, the entirety of which is incorporated by reference herein.

BACKGROUND OF THE INVENTION

Natural gas resources vary significantly in compositions. Natural gas contains mostly $CH_4$, but usually also contains various amounts of impurities (e.g. $CO_2$, $H_2S$, $N_2$, heavier hydrocarbons, and water). The concentration of these impurities in natural gas must be reduced to certain level before transportation and distribution. $CO_2$ is the primary impurity in most natural gas resources, and may exceed 50% in some wells under high pressure. Polymers are state-of-the-art membrane materials for $CO_2$ removal from natural gas. Un-crosslinked polymers may be swelled and dilated under high concentration of strongly sorbing penetrant (e.g. $CO_2$ and heavier hydrocarbons). This phenomenon is called plasticization and usually leads to increased membrane permeability and substantially reduced membrane permselectivity.

As a result, un-crosslinked polymers are usually incapable of processing high pressure natural gas with high level of $CO_2$. The problem of membrane plasticization is not limited to the treatment of natural gas. Rather, membrane plasticization may occur in any gas separation application when the gas stream being treated contains a high partial pressure of the selectively sorbed gas component or components. Therefore, plasticization may prevent effective commercial separation of many gases. Plasticization, i.e. swelling of the membrane and the resultant loss in permselectivity, has also been observed in certain carbon molecular sieve (CMS) membranes, as evidenced by, for example, Octavio Salinas et al., *High-performance carbon molecular sieve membranes for ethylene/ethane separation derived from intrinsically microporous polyimide*, Journal of Membrane Science, vol. 500, pages 115-123 (2006).

In the absence of plasticization, a substantial loss of both membrane permeability and permselectivity would be expected to occur during aggressive gas separation applications due to potential saturation of the micropores. Where the partial pressure of the selectively sorbed gas component(s) is high, it would be expected that the micropores in a CMS membrane may become saturated with the sorbed gases in a relatively short amount of time. Under high $CO_2$ partial pressures, for example, it would be expected that large amounts of $CO_2$ would be relatively quickly absorbed/adsorbed into the micropores of the CMS membrane, which would decrease the pore sizes and reduce the permeability/permeance of the CMS membrane. Thus, one would expect to observe a relatively rapid reduction in both permeability/permeance and permselectivity during treatment of a gas stream in which the sorbed gas component(s), such as $CO_2$, has a high partial pressure. Severe loss in membrane performance due to saturation has been observed, for example, in Cheryl W. Jones & William J. Koros, *Carbon molecular sieve gas separation membranes—II. Regeneration following organic exposure*, Carbon, vol. 32, issue 8, pages 1427-1432 (1994).

SUMMARY OF THE INVENTION

A first aspect of the present disclosure is directed to a process for separating at least first gas component and a second gas component by contacting a gas stream comprising at least a first gas component and a second gas component with a carbon molecular sieve (CMS) membrane to produce a retentate stream having a reduced concentration of the first gas component, and a permeate stream having an increased concentration of the first gas component, and wherein the partial pressure of the first gas component in the gas stream is high. For example, the partial pressure of the first gas component n the gas stream may be at least 20 bar, alternatively at least 30 bar, alternatively at least 40 bar, alternatively at least 50 bar, alternatively at least 60 bar, alternatively at least 70 bar, alternatively at least 80 bar, alternatively at least 90 bar. Despite the aggressive conditions, i.e. the high partial pressure of the sorbed gas component(s), the selectivity of the carbon molecular sieve membrane is not substantially reduced by plasticization or saturation. For instance, the selectivity of the carbon molecular sieve membrane during the contacting step should be at least 80% of the selectivity of the carbon molecular sieve membrane when contacted with a gas stream in which the partial pressure of the first gas component is 10 bar or less under the same conditions, preferably at least 85%, preferably at least 90%, preferably at least 95%. It should be noted that while the high-pressure separation process may be a commercial process, the low-pressure (i.e., 10 bar or less partial pressure) separation process that is performed for purposes of comparison may be a laboratory scale replication of the commercial process and still be considered to occur under the same conditions.

In some embodiments, the first gas component may comprise $CO_2$, $H_2S$, or a mixture thereof and the second gas component may comprise $CH_4$. For instance, in some embodiments, the process may be used to aggressively separate acid gases from a natural gas stream. In other embodiments, the first gas component may comprise an olefin ethylene, propylene, etc.) or a mixture of olefins and the second gas component may comprise a paraffin (e.g. ethane, propane, etc.) or a mixture of paraffins. In other embodiments, the first gas component may comprise $CO_2$ and the second gas component may comprise $N_2$. In each of these embodiments, the first gas component, the second gas component, or both may also comprise additional unlisted gas species. In some embodiments, the feed gas stream and the retentate stream may be brought to and/or kept at supercritical conditions during contact with the CMS membrane.

A second aspect of the present disclosure is directed to a process for separating at least $CO_2$ from a natural gas stream by contacting the natural gas stream with a carbon molecular sieve (CMS) membrane to produce a retentate stream having a reduced concentration of $CO_2$, and a permeate stream having an increased concentration of $CO_2$, and wherein the partial pressure of the $CO_2$ component in the natural gas stream is high. For example, the partial pressure of the $CO_2$ component in the natural gas stream may be at least 20 bar, alternatively at least 30 bar, alternatively at least 40 bar, alternatively at least 50 bar, alternatively at least 60 bar, alternatively at least 70 bar, alternatively at least 80 bar, alternatively at least 90 bar. Despite the aggressive conditions, i.e. the high partial pressure of the $CO_2$, the selectivity of the carbon molecular sieve membrane is not substantially reduced by plasticization or saturation. For instance, the selectivity of the carbon molecular sieve membrane during the contacting step should be at least 80% of the selectivity of the carbon molecular sieve membrane when contacted with a natural gas stream in which the partial pressure of $CO_2$ is 10 bar or less under the same conditions, preferably at least 85%, preferably at least 90%, preferably at least 95%. It should be noted that while the high-pressure separation process may be a commercial process, the low-pressure (i.e., 10 bar or less partial pressure separation process that is performed for purposes of comparison may be a laboratory scale replication of the commercial process and still be considered to occur under the same conditions.

In some embodiments, the natural gas stream may also comprise ethane, propane, butane isomers, pentane isomers, hexane isomers, hepta e isomers, benzene, toluene, ethylbenzene, xylene isomers, or any combination of the above. In some embodiments, contacting a natural gas stream with the carbon molecular sieve membrane may occur at a temperature between 50° C. and 100° C. In some embodiments, both the natural gas stream and the retentate stream may be brought to and/or kept at supercritical conditions during contact with the CMS membrane.

A third aspect of the present disclosure is directed to a process for separating at least a first gas component and a second gas component by contacting a feed stream comprising at least a first component and a second component with a carbon molecular sieve (CMS) membrane to produce a retentate stream having a reduced concentration of the first component, and a permeate stream having an increased concentration of the first component, wherein the feed stream is at a temperature and pressure in the supercritical region and the retentate stream is at a temperature and pressure in the supercritical region during contact with the CMS.

In some embodiments, the first gas component may comprise $CO_2$, $H_2S$, or a mixture thereof and the second gas component may comprise $CH_4$. For instance, in some embodiments, the process may be used to aggressively separate acid gases from a natural gas stream. In other embodiments, the first gas component may comprise an olefin (e.g. ethylene, propylene, etc.) or a mixture of olefins and the second gas component may comprise a paraffin (e.g. ethane, propane, etc.) or a mixture of paraffins. In other embodiments, the first gas component may comprise $CO_2$ and the second gas component may comprise $N_2$. In each of these embodiments, the first gas component, the second gas component, or both may also comprise additional unlisted gas species.

The carbon molecular sieve (CMS) membrane utilized in any of the above-described aspects may be an asymmetric hollow fiber membrane. The carbon molecular sieve (CMS) membrane utilized in any of the above-described aspects may be prepared by providing a polymer precursor, and heating said precursor to a temperature at which pyrolysis byproducts are evolved.

Prior to the heating step, the poly precursor may optionally be contacted with a solution comprising a modifying agent. In some embodiments, the modifying agent may be a compound having the formula $R^1R^2R^3R^4Si$, where each of $R^1$, $R^2$, $R^3$, and $R^4$ are independently. $C_1$-$C_6$ alkyl or alkenyl, alkoxy, or halogen; with the proviso that the compound contains at least one $C_1$-$C_6$ alkyl or alkenyl substituent and at least one alkoxy or halogen substituent. For instance, in some embodiments, the modifying agent may be vinyl trimethoxy silane. In other embodiments, the modifying agent may be a compound having the formula $R^1R^2R^3R^4M$, where M is a metal and where each of $R^1$, $R^2$, $R^3$, and $R^4$ are independently $C_1$-$C_6$ alkyl or alkenyl, alkoxy, or halogen, with the proviso that the compound contains at least one $C_1$-$C_6$ alkyl or alkenyl substituent and at least one alkoxy or halogen substituent. M may be, for example, selected from the group consisting of Ge, B, Al, Ti, V, Fe, and a combination thereof.

In some embodiments the polymer precursor may comprise a rigid, glassy polymer, such as a polyimide or polysulfone. For instance, the polyimide may be selected from the group consisting of Matrimid 5218 and 6FDA/BPDA-DAM. In some embodiments, the pyrolysis temperature may be between about 500° and 900° C. and in some embodiments the pyrolysis may occur under an atmosphere having an oxygen concentration between 1 ppm and 50 ppm.

BRIEF DESCRIPTION OF THE DRAWINGS

A clear conception of the advantages and features of one or more embodiments will become more readily apparent by reference to the exemplary, and therefore non-limiting, embodiments illustrated in the drawings.

DETAILED DESCRIPTION OF THE INVENTION

Membranes are widely used for the separation of gases and liquids, including for example, separating acid gases, such as $CO_2$ and $H_2S$ from natural gas. Gas transport through such membranes is commonly modeled by the sorption-diffusion mechanism. Specifically, gas molecules sorb into the membrane at the upstream, and finally desorb from the membrane at the downstream. Two intrinsic properties are commonly used to evaluate the performance of a membrane material; "permeability" and "selectivity." Permeability is hereby defined as a measure of the intrinsic productivity of a membrane material; more specifically, it is the partial pressure and thickness normalized flux, typically measured in Barrer. Permeance, which is sometimes used in place of permeability, measures the pressure-normalized flux of a given compound. Selectivity, meanwhile, is a measure of the ability of one gas to permeate through the membrane versus a different gas; for example, the permeability of $CO_2$ versus $CH_4$, measured as a unit-less ratio.

Currently, polymeric membranes are well studied and widely available for gaseous separations due to easy processability and low cost. CMS membranes, however, have been shown to have attractive separation performance properties exceeding that of polymeric membranes. CMS membranes are typically produced through thermal pyrolysis of polymer precursors. Many polymers have been used to produce CMS membranes in fiber and dense film form. Polyimides have a high glass transition temperature, are easy to process, and have one of the highest separation performance properties among other polymeric membranes, even prior to pyrolysis.

Because carbon molecular sieve (CMS) membranes can be prepared to selectively sorb a first gas component from a gas mixture, they may be used for a wide range of gas separation applications. For instance, in various embodiments, CMS membranes may be configured for the separation particular gases, including but not limited to $CO_2$ and $CH_4$, $H_2S$ and $CH_4$, $CO_2/H_2S$ and $CH_4$, $CO_2$ and $N_2$, $O_2$ and $N_2$, $N_2$ and $CH_4$, He and $CH_4$, $H_2$ and $CH_4$, $H_2$ and $C_2H_4$, ethylene and ethane, propylene and propane, and ethylene/propylene and ethane/propane, each of which may be performed within a gas stream comprising additional components. One of the many gas separation applications in which CMS membranes may be particularly suitable is in the separation of acid gas components—$CO_2$, $H_2S$, or a combination thereof—from a hydrocarbon-containing gas stream such as natural gas. The CMS membranes may be prepared so as to selectively sorb these acid gases, producing a permeate stream having an increased concentration of acid gases and a retentate stream having a reduced concentration of acid gases.

Figure 1A:
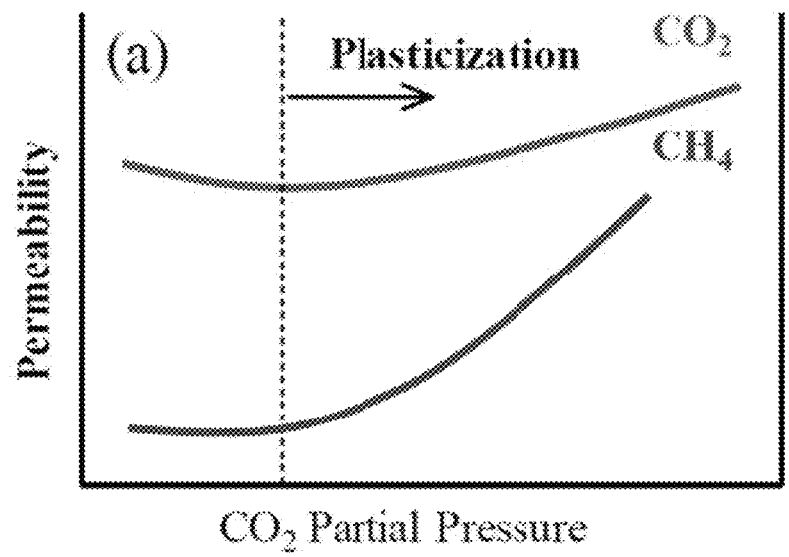
FIG. 1A is an illustration of $CO_2$ permeability increase as a result of plasticization.
Figure 1B:
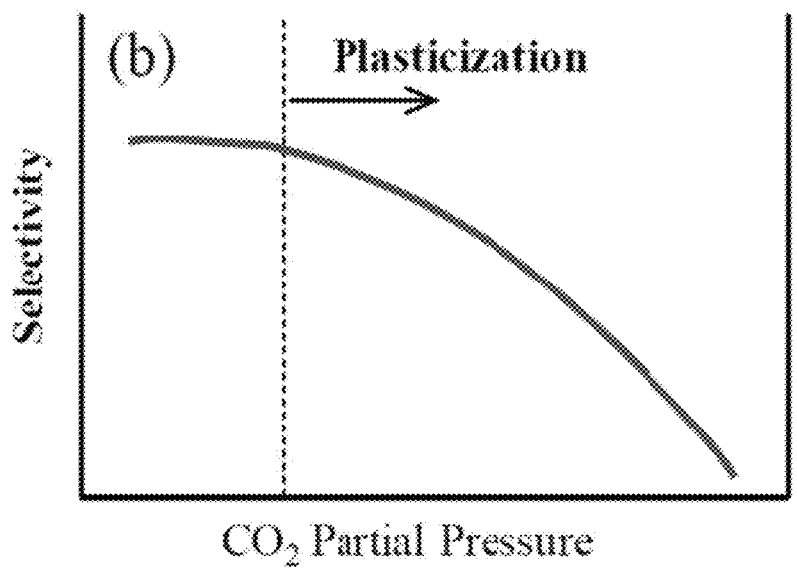
FIG. 1B is an illustration of $CO_2$/$CH_4$ selectivity reduction as a result of plasticization.

Gas separation is often presently performed using polymeric membranes. However, when the gas stream being treated/separated contains a high partial pressure of the selectively sorbed gas component or components, polymeric membranes tend to undergo plasticization. As the polymeric membrane undergoes plasticization, the porous microstructure of the polymer breaks down. As a result, selectivity of the membrane drops significantly, as gas components other than the desired component are able to pass through the membrane. This effect is shown in FIGS. 1A and 1B.

Plasticization, as used herein, occurs when a strongly sorbing penetrant reaches a concentration such that it swells and dilates the membrane. For polymers, this typically means increased mobility of polymer chain segments, thereby increased diffusion coefficients of all penetrants and reduction in diffusion selectivity and therefore, membrane permselectivity. Gases with high critical temperature, such as $CO_2$ and condensable hydrocarbons commonly present in raw natural gas, are known to strongly interact with polymers and can potentially cause plasticization. Plasticization, i.e., swelling of the membrane and the resulting loss in permselectivity, has also been found to occur in certain carbon molecular sieve membranes. See, for example, Octavio Salinas et al., *High-performance carbon molecular sieve membranes for ethylene/ethane separation derived from intrinsically microporous polyimide*, Journal of Membrane Science, vol. 500, pages 115-123 (2006).

It has surprisingly been found that the CMS membranes prepared according to the present disclosure are resistant to plasticization and therefore are suitable for gas separation even under conditions where the sorbed gas component(s) have a high partial pressure within the gas stream being treated, i.e. separated. It has also surprisingly been found that the CMS membranes prepared according to the present disclosure do not undergo rapid saturation and thus are not subject to a substantial decrease in permeability and/or selectivity due to saturation where the sorbed gas component(s) have a high partial pressure within the gas stream being treated, i.e. separated. Because the CMS membranes prepared according to the present disclosure do not undergo plasticization or rapid saturation, the selectivity of the CMS membranes is substantially unchanged by the high partial pressures of sorbed gas(es) during the gas separation process, i.e., the CMS membranes do not undergo drastic decreases in selectivity, such as those shown in FIG. 1B, at high partial pressures of sorbed species.

For instance, when the presently disclosed CMS membranes are used for the separation of $CO_2$ from natural gas ($CH_4$) having high partial pressures of $CO_2$, the $CO_2/CH_4$ selectivity of the CMS membrane is substantially the same as the $CO_2/CH_4$ selectivity of the CMS membrane when subjected to low partial pressures of $CO_2$. For instance, the selectivity of the CMS membrane under high $CO_2$ partial pressure (e.g. at least 20 bar, at least 30 bar, at least 40 bar, at least 50 bar, at least 60 bar, at least 70 bar, or at least 80 bar) may be at least 80%, more desirably at least 85%, more desirably at least 90%, more desirably at least 95% of the selectivity of the CMS membrane under low $CO_2$ partial pressure (e.g. 10 bar or less, about 10 bar, about 9 bar, about 8 bar, about 7 bar, about 6 bar, or about 5 bar). For example, the experimental results in Table 1 demonstrate that the selectivities of the CMS membranes under a $CO_2$ partial pressure of 750 psia (or about 50 bar) are within 90% and 95% of the selectivities of the CMS membrane when subjected to $CO_2$ and $CH_4$ single gas permeation under at 100 psia (or about 7 bar).

Figure 2A:
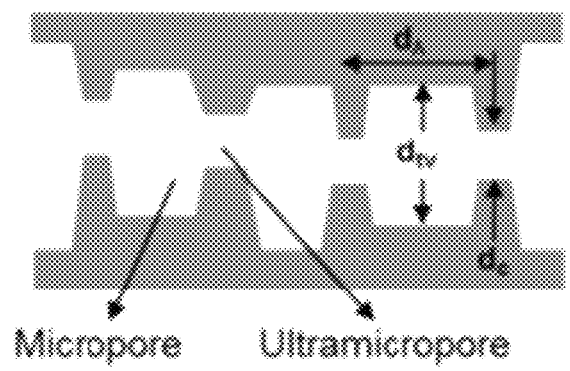
FIG. 2A is an illustration showing the "slit-like" pore structure of carbon molecular sieve membranes.
Figure 2B:
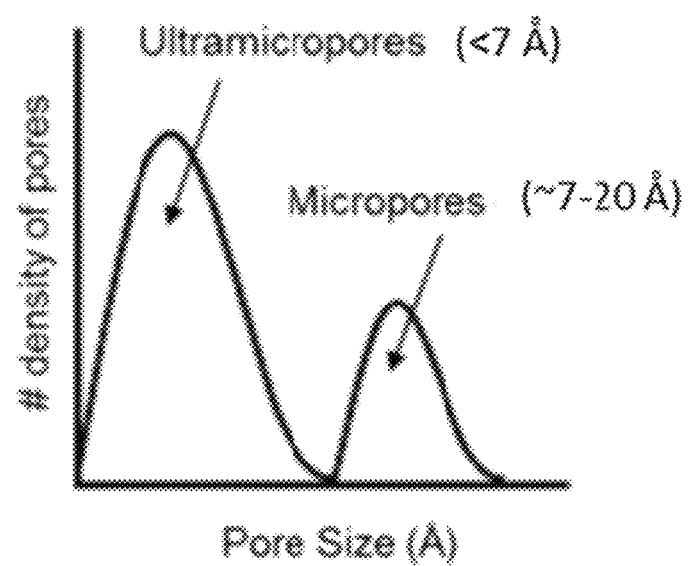
FIG. 2B is an illustration showing the bimodal pore size distribution of carbon molecular sieve membranes.

CMS membranes can be formed into asymmetric hollow fibers, by controlled pyrolysis of polymeric precursor hollow fiber membranes, and are capable of delivering simultaneously attractive productivity and separation efficiency without compromising scalability. CMS pore structure is formed by packing imperfections of high disordered and disoriented $sp^2$-hybridized graphene-like sheets. An illustration visualizing CMS porous structure is shown in FIG. 2A. As shown in FIG. 2B, the pore structure of a CMS membrane can be represented by a bimodal pore size distribution. Micropores (7 Å<d<20 Å) provide the majority of surface area for sorption and are responsible for the membrane's high permeability. On the other hand, ultramicropores (d<7 Å) connecting micropores control diffusivity and consequently diffusion selectivity.

U.S. Pat. Nos. 8,486,179, 9,211,504, and U.S. Patent Application Publication No. 2015/009445 A1, which are incorporated herein by reference in their entireties, describe examples of methods of synthesizing CMS membranes.

Asymmetric Hollow Fiber Membranes

Carbon molecular sieve (CMS) membranes have shown great potential for the separation of gases, such as for the removal of carbon dioxide ($CO_2$) and other acid gases from natural gas streams. Asymmetric CMS hollow fiber membranes are preferred for large scale, high pressure applications.

Asymmetric hollow fiber membranes have the potential to provide the high fluxes required for productive separation due to the reduction of the separating layer to a thin integral skin on the outer surface of the membrane. The asymmetric hollow morphology, i.e. a thin integral skin supported by a porous base layer or substructure, provides the fibers with strength and flexibility, making them able to withstand large transmembrane driving force pressure differences. Additionally, asymmetric hollow fiber membranes provide a high surface area to volume ratio.

Asymmetric CMS hollow fiber membranes comprise a thin and dense skin layer supported by a porous substructure. Asymmetric polymeric hollow fibers, or precursor fibers, are conventionally formed via a dry-jet/wet-quench spinning process, also known as a dry/wet phase separation process or a dry/wet spinning process. The precursor fibers are then pyrolyzed at a temperature above the glass transition temperature of the polymer to prepare asymmetric CMS hollow fiber membranes.

The polymer solution used for spinning of an asymmetric hollow fiber is referred to as dope. During spinning, the dope surrounds an interior fluid, which is known as the bore fluid. The dope and bore fluid are coextruded through a spinneret into an air gap during the "dry-jet" step. The spun fiber is then immersed into an aqueous quench bath in the "wet-quench" step, which causes a wet phase separation process to occur. After the phase separation occurs, the fibers are collected by a take-up drum and subjected to a solvent exchange process.

The solvent exchange process is an extremely important step in the membrane fabrication process. If the porous precursor fibers contain water at the time they are subjected to high temperatures, for instance during drying or pyrolysis, removal of the water causes significant changes to the structure and properties of the fiber and of the resulting CMS membrane. The high capillary forces associated with removal of water within the small radii of the pores close to the skin cause a densification of the structure in this region, which results in a less permeable membrane. To prevent this, the solvent exchange process replaces the water that is present in the porous substructure of the precursor fiber with a fluid having a lower surface tension.

A conventional solvent exchange process involves two or more steps, with each step using a different solvent. The first step or series of steps involves contacting the precursor fiber with one or more solvents that are effective to remove the water in the membrane. This generally involves the use of one or more water-miscible alcohols that are sufficiently inert to the polymer. The aliphatic alcohols with 1-3 carbon atoms, i.e. methanol, ethanol, propanol, isopropanol, and combinations of the above, are particularly effective as a first solvent. The second step or series of steps involves contacting the fiber with one or more solvents that are effective to replace the first solvent with one or more volatile organic compounds having a low surface tension. Among the organic compounds that are useful as a second solvent are the $C_5$ or greater linear or branched-chain aliphatic alkanes.

The solvent exchange process typically involves soaking the precursor fibers in a first solvent for a first effective time, which can range up to a number of days, and then soaking the precursor fibers in a second solvent for a second effective time, which can also range up to a number of days. Where the precursor fibers are produced continuously, such as in a commercial capacity, a long precursor fiber may be continuously pulled through a series of contacting vessels, where it is contacted with each of the solvents. The solvent exchange process is generally performed at room temperature.

The precursor fibers are then dried by heating to temperature above the boiling point of the final solvent used in the solvent exchange process and subjected to pyrolysis in order to form asymmetric CMS hollow fiber membranes.

The choice of polymer precursor, the formation and treatment of the precursor fiber prior to pyrolysis, and the conditions of the pyrolysis all influence the performance properties of an asymmetric CMS hollow fiber membrane.

Precursor Fibers

The asymmetric polymer precursor fiber may comprise any polymeric material that, after undergoing pyrolysis, produces a CMS membrane that permits passage of the desired gases to be separated, for example carbon dioxide and natural gas, and in which at least one of the desired gases permeates through the CMS fiber at different diffusion rate than other components.

For instance, the polymer may be any rigid, glassy polymer (at room temperature) as opposed to a rubbery polymer or a flexible glassy polymer. Glassy polymers are differentiated from rubbery polymers by the rate of segmental movement of polymer chains. Polymers in the glassy state do not have the rapid molecular motions that permit rubbery polymers their liquid-like nature and their ability to adjust segmental configurations rapidly over large distances (>0.5 nm). Glassy polymers exist in a non-equilibrium state with entangled molecular chains with immobile molecular backbones in frozen conformations. The glass transition temperature (Tg) is the dividing point between the rubbery or glassy state. Above the Tg, the polymer exists in the rubbery state; below the Tg, the polymer exists in the glassy state. Generally, glassy polymers provide a selective environment for gas diffusion and are favored for gas separation applications. Rigid, glassy polymers describe polymers with rigid polymer chain backbones that have limited intramolecular rotational mobility and are characterized by having high glass transition temperatures. Preferred rigid, glassy polymer precursors have a glass transition temperature of at least 200° C.

In rigid, glassy polymers, the diffusion coefficient tends to control selectivity, and glassy membranes tend to be selective in favor of small, molecules. For example, preferred membranes may be made from rigid, glassy polymer materials that will pass carbon dioxide, hydrogen sulfide and nitrogen preferentially over methane and other light hydrocarbons. Such polymers are well known in the art and include polyimides, polysulfones and cellulosic polymers.

The polyimides are preferred polymers precursor materials. Suitable polyimides include, for example, Ultem®, 1000, Matrimid® 5218, 6FDA/BPDA-DAM, 6FDA-6FpDA, and 6FDA-IPDA. The polyimide commercially sold as Matrimid® 5218 is a thermoplastic polyimide based on a specialty diamine, 5(6)-amino-1-(4'aminophenyl)-1,3,-trimethylindane. Its structure is:

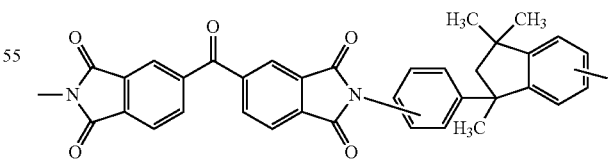

The Matrimid® 5218 polymers used in the Examples were obtained from Huntsman International LLC. 6FDA/BPDA-DAM is a polymer made up of 2,4,6-Trimethyl-1,3-phenylene diamine (DAM), 3,3,4,4-biphenyl tetracarboxylic dianhydride (BPDA), and 5,5-[2,2,2-trifluoro-1-(trifluoromethyl)ethylidene]bis-1,3-isobenzofurandione (6FDA), and having the structure:

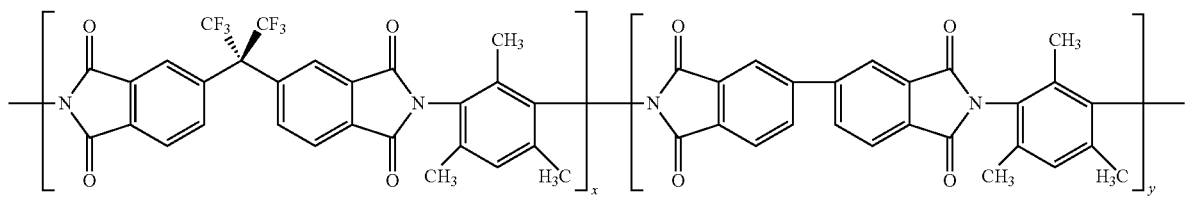

To obtain the above mentioned polymers one can use available sources or synthesize them. For example, such a polymer is described in U.S. Pat. No. 5,234,471, the contents of which are hereby incorporated by reference.

Although polyimide polymers are used in the examples, it is understood that the polyimides are merely examples of rigid, glassy polymers. Accordingly, the preparation of CMS membranes from the polyimides used in the examples is exemplary and representative of the preparation of CMS membranes from rigid, glassy polymers as a class of materials. Similarly, the use of CMS membranes prepared from polyimide precursors for the separation of gases, as demonstrated in the examples, is exemplary and representative of the gas separation performance of CMS membranes prepared from rigid, glassy polymers as a class of materials.

Examples of other suitable precursor polymers include polysulfones; poly(styrenes), including styrene-containing copolymers such as acrylonitrilestyrene copolymers, styrene-butadiene copolymers and styrene-vinylbenzylhalide copolymers: polycarbonates; cellulosic polymers, such as cellulose acetate-butyrate, cellulose propionate, ethyl cellulose, methyl cellulose, nitrocellulose, etc.; poly-amides and polyimides, including aryl polyamides and aryl polyimides; polyethers; polyetherimides; polyetherketones; poly(arylene oxides) such as poly(phenylene oxide) and poly(xylene oxide); poly(esteramide-diisocyanate); polyurethanes; polyesters (including polyarylates), such as poly(ethylene terephthalate), poly(alkyl methacrylates), poly(acrylates), poly(phenylene terephthalate), etc.; polypyrrolones; polysulfides; polymers from monomers having alpha-olefinic unsaturation other than mentioned above such as poly(ethylene), poly(propylene), poly(butene-1), poly(4-methyl pentene-1), polyvinyls, e.g., poly(vinyl chloride), polyvinyl fluoride, poly(vinylidene chloride), poly(vinylidene fluoride), poly(vinyl alcohol), poly(vinyl esters) such as polyvinyl acetate) and polyvinyl propionate), poly(vinyl pyridines), poly(vinyl pyrrolidones), polyvinyl ethers), poly (vinyl ketones), polyvinyl aldehydes such as poly(vinyl formal) and poly(vinyl butyral), polyvinyl amides), polyvinyl amines), poly(vinyl urethanes), polyvinyl ureas), polyvinyl phosphates), and polyvinyl sulfates); polyallyls; poly (benzobenzimidazole); polyhydrazides; polyoxadiazoles; polytriazoles; poly(benzimidazole); polycarbodiimides; polyphosphazines; etc., and interpolymers, including block interpolymers containing repeating units from the above such as terpolymers of acrylonitrile-vinyl bromide-sodium salt of para-sulfophenylmethallyl ethers; and grafts and blends containing any of the foregoing. Typical substituents providing substituted polymers include halogens such as fluorine, chlorine and bromine; hydroxyl groups; lower alkyl groups; lower alkoxy groups; monocyclic aryl; lower acyl groups and the like.

The asymmetric polymer precursor fiber may be a composite structure comprising a first polymer material supported on a porous second polymer material. Composite structures may be formed by using more than one polymer material as the dope during the asymmetric hollow fiber spinning process.

Modifying Agents

The term modifying agent, as used herein, refers to a compound that is capable of undergoing a reaction within the pores of a polymer precursor fiber to form a morphology stabilizer without otherwise adversely affecting the mechanical properties of the fiber.

Preferred modifying agents are those that undergo a polycondensation reaction to form siloxane bridges. For example, the modifying agent may be a silane having the general formula $R^1R^2R^3R^4Si$, where each of $R^1$, $R^2$, $R^3$, and $R^4$ are independently $C_1$-$C_6$ alkyl or alkenyl, alkoxy, or halogen, with the proviso that the silane contains at least one $C_1$-$C_6$ alkyl or alkenyl substituent and at least one alkoxy or halogen substituent. The at least one alkoxy or halogen substituent provides the silane with the capability of forming a chain-like network of siloxane bonds. The at least one $C_1$-$C_6$ alkyl or alkenyl substituent provides that the treatment of a fiber with the modifying agent does not render the fiber brittle. Subject to this proviso, each of the substituents can be varied in order to provide the silane with desired properties. For example, by selection of the substituent groups, one may be able to alter the porosity of the resulting morphology stabilizer.

In some preferred embodiments, vinyl trimethoxy silane (VTMS) is used as the modifying agent for precursor treatment, but other silanes can also be employed as a modifying agent. The modifying agent, for example, may be a monosilane or an oligosiloxane such as a disiloxane or a trisiloxane. For instance, in various embodiments, the modifying agent may be selected from the group consisting of vinyl trimethoxysilane, vinyl triethoxysilane, vinyl dimethoxychlorosilane, vinyl diethoxychlorosilane, vinyl methoxydichlorosilane, vinyl ethoxydichloro silane, vinyl trichloro silane, vinyl pentamethoxydisiloxane, divinyl tetramethoxydisiloxane, and combinations thereof. In various particularly preferred embodiments, the at least one alkoxy or halogen substituent comprises methoxy or ethoxy. In various particularly preferred embodiments, the at least one $C_1$-$C_6$ alkyl or alkenyl substituent comprises vinyl. Particularly preferred modifying agents include vinyl trimethoxy silane, vinyl triethoxy silane, ethane trimethoxy silane, and methyl trimethoxy silane.

Other modifying agents include those that undergo a polycondensation reaction to form metal-oxo and/or metal oxycarbide bonds. For example, the modifying agent may be a metal alkoxide having the general formula $R^1R^2R^3R^4M$, where M is a metal and where each of $R^1$, $R^2$, $R^3$, and $R^4$ are independently $C_1$-$C_6$ alkyl or alkenyl, alkoxy, or halogen, with the proviso that the metal alkoxide contain at least one $C_1$-$C_6$ alkyl or alkenyl substituent and at least one alkoxy or halogen substituent. The at least one alkoxy or halogen substituent provides the metal alkoxide with the capability of forming a chain-like network of metal-oxo and/or metal oxycarbide bonds. The at least one $C_1$-$C_6$ alkyl or alkenyl substituent provides that the treatment of a fiber with the metal alkoxide does not render the fiber brittle. Subject to this proviso, each of the substituents can be varied in order to provide the metal alkoxide with desired properties. For example, by selection of the substituent groups, one may be able to alter the porosity of the resulting morphology stabilizer. In preferred embodiments, the metal M is selected from the group consisting of Ge, B, Al, Ti, V. Fe, and combinations thereof.

Treatment and Pyrolysis Conditions

In modifying a polymer precursor fiber to prepare a substantially non-collapsed, asymmetric CMS hollow fiber membrane, the process comprises the steps of providing the polymer precursor, providing a contacting solution comprising a modifying agent (which is present in the solution at a concentration 1.00 wt % or less than 100 wt %), and allowing at least a portion of the polymer precursor to contact at least a portion of the contacting solution comprising the modifying agent to create a modified polymer precursor that, when pyrolyzed, produces a substantially non-collapsed, asymmetric modified CMS hollow fiber membrane. Preferably, the polymer precursor is soaked in a solution comprising the modifying agent at a desired concentration for a period of time sufficient to allow the modifying agent to enter the substructure pores of the precursor fiber. Preferably, the period of time is from about 30 minutes to about 24 hours.

The solution containing the modifying agent need not contact an end of the hollow precursor fiber in order to enter the substructure pores of the precursor fiber. Rather, it has been found that the modifying agent may penetrate the outer skin of the precursor fiber in a radial direction, and enter the substructure pores of the fiber in this manner.

The contacting of a precursor fiber with a modifying agent preferably takes place at room temperature. However, in some additional embodiments, the contacting temperature may be held within a range selected from approximately 20° C. to approximately the polymer precursor glass transition temperature; from approximately 100° C. to approximately the polymer precursor glass transition temperature; and from approximately 100° C. to approximately 250° C.

In various embodiments, the reaction of the modifying agent to form a morphology stabilizer may require the addition of a catalyst. For example, when vinyl triethoxy silane is used as the modifying agent, it may be desirable to add a catalyst to promote the sol-gel reaction. This is due to the slow reaction of ethoxy groups compared to the methoxy groups of, for example, VTMS. The sol-gel reaction can be promoted through the addition of an acid, such as a mineral acid, as it is known in the art that a sot-gel reaction is often significantly increased under acidic conditions. Preferred acid catalysts include any readily available mineral acid, such as hydrochloric acid, sulfuric acid, nitric acid, phosphoric acid, boric acid, hydrofluoric acid, hydrobromic acid, perchloric acid, and combinations thereof.

Once the precursor fiber has been in contact with the modifying agent, e.g. by soaking in a solution containing the modifying agent at a selected concentration, the treated precursor fiber is contacted with moisture, such as by placing the fiber under a moisture-containing atmosphere. The moisture-containing atmosphere may be one that has a relative humidity between about 50% and 100%. The precursor fibers are preferably held under the moisture-containing atmosphere for a period of time between about 1 hour and 60 hours.

The treated precursor fibers are then dried and pyrolyzed. The pyrolysis is advantageously conducted under an inert atmosphere. The pyrolysis temperature may be between about 500° and about 900° C.; alternatively, the pyrolysis temperature may be between about 500° and about 800° C.; alternatively, the pyrolysis temperature may be between about 500° and about 700° C.; alternatively, the pyrolysis temperature may be between about 500° and 650° C.; alternatively, the pyrolysis temperature may be between about 500° and 600° C.; alternatively, the pyrolysis temperature may be between about 500° and 550° C.; alternatively, the pyrolysis temperature may be between about 550° and about 700° C.; alternatively, the pyrolysis temperature may be between about 550° and about 650° C. alternatively the pyrolysis temperature may be between about 600° and about 700° C.; alternatively the pyrolysis temperature may be between about 600° and about 650° C. The pyrolysis temperature is typically reached by a process in which the temperature is slowly ramped up. For example, when using a pyrolysis temperature of 650° C., the pyrolysis temperature may be achieved by increasing the temperature from 50° C. to 250° C. at a ramp rate of 13.3° C./min, increasing the temperature from 250° C. to 635° C. at a ramp rate of 3.85° C./min, and increasing the temperature from 635° C. to 650° C. at a ramp rate of 0.25° C./min. Once the pyrolysis temperature is reached, the fibers are heated at the pyrolysis temperature for a soak time, which may be a number of hours.

The polymer precursor fibers may also be bundled and pyrolyzed as a bundle in order produce a large amount of modified CMS hollow fiber membranes in a single pyrolysis run. Although pyrolysis will generally be referred to in terms of pyrolysis of a precursor fiber, it should be understood that any description of pyrolysis used herein is meant to include pyrolysis of precursor fibers that are bundled as well as those that are non-bundled.

In various embodiments, treatment of the polymer precursor fiber may be coupled with the solvent exchange process. After the precursor fibers are formed, such as by the dry-jet, wet-quench method, the fibers are subjected to a process known as solvent exchange. In order to maintain the porosity of the fibers through drying, it is necessary to remove the water contained within the pores of the membrane. Accordingly, the solvent exchange process replaces the water that is present in the porous substructure of the fiber with an organic compound having a low surface tension. The precursor fiber is subjected to the solvent exchange process for a time that is effective to allow the organic compound to replace the water that is present in the pores of the fiber.

Solvent exchange preferably involves two or more steps, with each step using a different solvent exchange material. By way of example, a conventional solvent exchange process includes removing the water in the membrane with a first solvent and then replacing the alcohol with a second solvent. The first step uses one or more solvent exchange materials comprising a water-miscible alcohol that is sufficiently inert to the polymer. Any compound that is effective for replacing water in the membrane is contemplated for use as a first solvent. The aliphatic alcohols with 1-3 carbon atoms, i.e. methanol, ethanol, propanol, isopropanol, and combinations of the above, are particularly effective as a first solvent exchange material.

The second step is effective to replace the alcohol with one or more volatile organic compounds having a low surface tension. Any organic solvent that has a sufficiently low surface tension to prevent damage to the membrane pores during heating is contemplated for use as a second solvent. Among the organic compounds that are particularly useful as a second solvent exchange material are the $C_5$ or greater linear or branched-chain aliphatic alkanes. Toluene has also been suggested for use as a second solvent. N-hexane has been found to be a particularly suitable organic compound for use as the second solvent exchange material. Advantageously, the first and second solvent exchange materials should be sufficiently nonreactive with the membrane so as to prevent any significant degradation of membrane properties.

Although the process described in this exemplary embodiment includes only two steps, the solvent exchange process may involve any number of steps and any number of solvents. A solvent exchange process may make use of any number of solvent exchange materials, with the solvent exchange material of each subsequent step being effective to replace the solvent exchange material of the preceding step.

It has presently been found that by using a solvent exchange material that includes an amount of a modifying agent, an asymmetric modified CMS hollow fiber membrane having enhanced gas permeance may be prepared. Since treatment of a precursor fiber with a modifying agent in order to restrict the substructure collapse may be performed in association with the solvent exchange process, a modified CMS hollow fiber membrane having enhanced gas permeance may be prepared without the need for an additional process step beyond those which are typically performed in the preparation of an asymmetric CMS hollow fiber membrane. The process of treating the precursor fiber with a modifying agent, as described herein, as part of the solvent exchange step may be referred to as an enhanced solvent exchange process.

Accordingly, in various embodiments, a modifying agent is added to the second solvent in the solvent exchange process. For instance, the modifying agent is added to an organic solvent that has a sufficiently low surface tension to maintain the membrane pores during drying. In one suitable embodiment, the organic solvent is n-hexane. The concentration of the modifying agent in the organic solvent may be selected as described in this specification.

In an enhanced solvent exchange process, the precursor fiber is soaked in a solution comprising an organic compound, such as n-hexane, and a modifying agent, such as VTMS, for a period of time that is effective to allow the modifying agent to react with a portion of the water in the pores of the fiber and the organic solvent to replace another portion of the water in the pores of the fiber. In this way, the precursor fibers acquire the benefits of treatment with the modifying agent without losing the benefits of the conventional solvent exchange process.

The ability of the modifying agent to penetrate the outer skin of the asymmetric precursor fiber renders it particularly attractive for treatment of the fiber during the solvent exchange process. In a commercial process, a precursor fiber is often conveyed through the solvent exchange material in a continuous manner. Accordingly, the ends of the fiber rarely, if ever, come into contact with the solvent exchange material. Thus, for effective treatment during the commercial manufacture of an asymmetric CMS hollow fiber membrane, the modifying agent reaches the substructure of the precursor fiber through the outer skin of the fiber.

Experimental Procedure

Formation of 6FDA/BPDA-DAM Precursor Hollow Fiber Membranes

Monolithic 6FDA/BPDA-DAM precursor hollow fiber membranes were formed using the "dry-jet/wet-quench" fiber spinning technique.

Formation of CMS Hollow Fiber Membranes

CMS hollow fiber membranes were formed by controlled pyrolysis of 6FDA/BPDA-DAM precursor hollow fibers using the heating protocol noted below under continuous purge (200 cc/min) of ultra-high-purity (UHP) Argon. Details of the pyrolysis set-up can be found elsewhere.

Heating Protocol:
1) 50° C. to 250° C. (13.3° C./min)
2) 250° C. to 535° C. (3.85° C./min)
3) 535° C. to 550° C. (0.25° C./min)
4) Thermal soak at 550° C. for 120 min
5) Cool down naturally Assembling of CMS Hollow Fiber Membrane Modules Assembling of CMS Hollow Fiber Membrane Modules Using the Duralco™ 4525 Epoxy:

The resin (100 parts) was mixed with the hardener (8 parts) and stirred vigorously at room temperature before being degassed in a sonication bath for 2 mins. The thick epoxy paste was poured into one side of the fiber module and allowed to cure at room temperature for 12 hours. The process was repeated for the other side of the fiber module. The epoxy was allowed to cure for another 12 hours at room temperature before permeation tests.

Assembling of CMS Hollow Fiber Membrane Modules Using the 3M DP-100 Epoxy:

The epoxy was first poured into one side of the fiber module through a mixing nozzle. After curing for 10 mins at room temperature, the process was repeated for the other side of the fiber module. The epoxy was allowed to cure for another 12 hours at room temperature before permeation tests.

Permeation Characterizations of CMS Hollow Fiber Membranes $CO_2/CH_4$ Single-Gas Permeation at 100 psia:

$CO_2/CH_4$ single gas permeation measurements were done at 35° C. with a constant-volume permeation system. The upstream pressure was ~100 psia and downstream was at vacuum.

Figure 3:
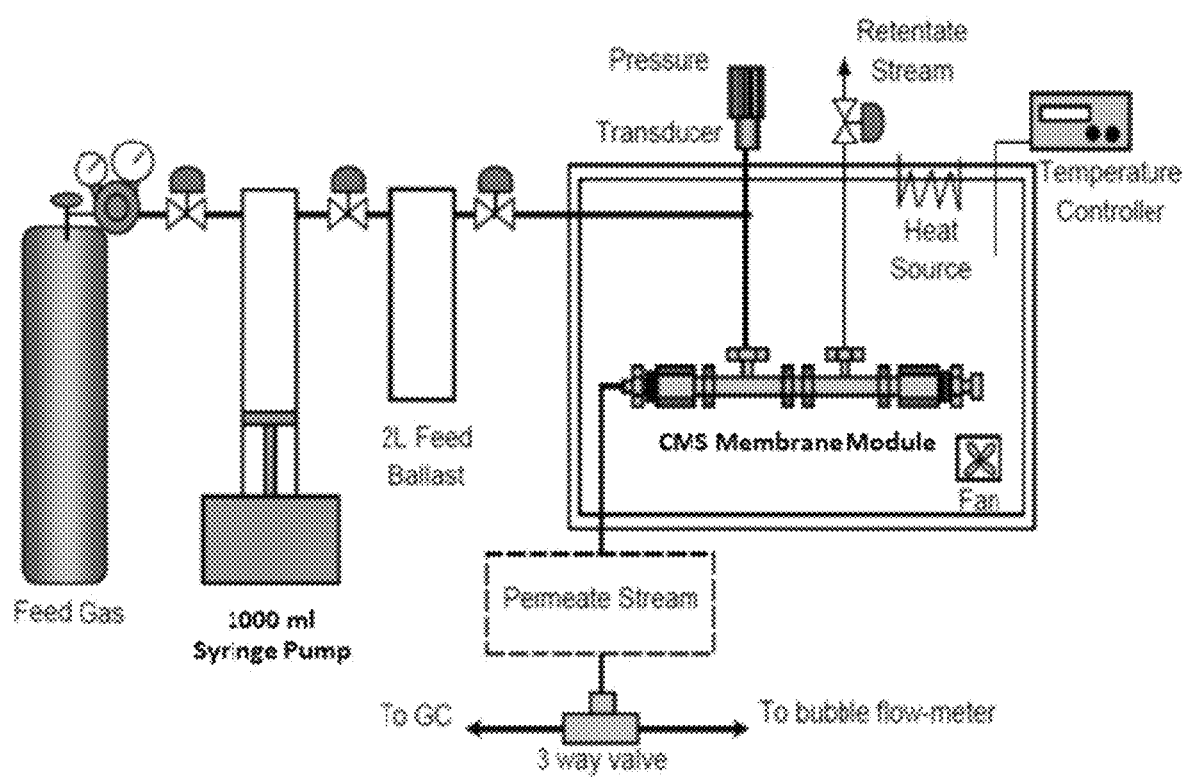
FIG. 3 is a schematic illustration of a high pressure (e.g. 1500 psia) equal-molar $CO_2$/$CH_4$ mixed-gas permeation system, such as the one used in the experiments disclosed herein.

Equal-Molar $CO_2/CH_4$ Mixed-Gas Permeation at 1500 psia:

Equal-molar $CO_2/CH_4$ mixed-gas gas permeation measurements were done at 35° C. with a constant-pressure permeation system, such as the one shown in FIG. 3. The upstream pressure was ~1500 psia (~103 bars) and downstream was at atmosphere. As shown in FIG. 3, a syringe pump was used to maintain the high pressure at membrane upstream. The stage-cut was kept below 1% by adjusting flowrate of membrane retentate. A Varian 450 GC was used to measure the compositions of membrane permeates. Membrane separation factors were calculated based on at least three GC injections.

Results and Discussion

High Pressure $CO_2/CH_4$ Mixed-Gas Permeation of CMS Hollow Fiber Membranes

Permeation data of CMS hollow fiber membranes pyrolyzed without and with 25 wt % VTMS pre-treatment[7] are summarized in Table 1.

TABLE 1

| Feed | P(CO$_2$)/GPU | α(CO$_2$/CH$_4$) |
|---|---|---|
| Without VTMS pre-treatment | | |
| CO$_2$/CH$_4$ single-gas permeation (100 psia) | 138 | 39 |
| Equal-molar CO$_2$/CH$_4$ mixed-gas permeation (1500 psia) | 81 | 36 |
| With VTMS (25 wt %) pre-treatment | | |
| CO$_2$/CH$_4$ single-gas permeation (100 psia) | 193 | 47 |
| Equal-molar CO$_2$/CH$_4$ mixed-gas permeation (1500 psia) | 93 | 49 |

Both modules were assembled with the Duralco™ 4525 epoxy. CO$_2$/CH$_4$ separation factors measured at 1500 psia are in general consistent with CO$_2$/CH$_4$ ideal selectivity measured at 100 psia. This suggests that the studied CMS hollow fiber membranes have excellent plasticization resistance under high pressure natural gas with high level of CO$_2$. The CMS hollow fiber membrane pyrolyzed with 25 wt % VTMS pre-treatment showed quite attractive natural gas separation performance at 1500 psia, with CO$_2$ permeance of 93 GPU and CO$_2$/CH$_4$ separation factor of 49.

Table 1 also shows that CO$_2$ permeances of the studied CMS hollow fibers were lower at 1500 psia. This can be explained by the shape of the Langmuir isotherm in CMS materials, which leads to reduced sorption coefficient as pressure increases. Additionally, it should be noted that both CO$_2$ permeance and CO$_2$/CH$_4$ separation factor were higher for the CMS hollow fiber pyrolyzed with 25 wt % VTMS pre-treatment.

The Effect of Epoxy on High Pressure CO$_2$/CH$_4$ Mixed-Gas Permeation Data of CMS Hollow Fiber Membranes Table 2 compares permeation data of CMS hollow fiber membrane modules assembled using the Duralco™ 4525 epoxy and the 3M DP-100 epoxy.

TABLE 2

| Feed | P(CO$_2$)/GPU | α(CO$_2$/CH$_4$) |
|---|---|---|
| Duralco ™ 4525 epoxy | | |
| CO$_2$/CH$_4$ single-gas permeation (100 psia) | 138 | 39 |
| Equal-molar CO$_2$/CH$_4$ mixed-gas permeation (1500 psia) | 81 | 36 |
| 3M DP-100 epoxy | | |
| CO$_2$/CH$_4$ single-gas permeation (100 psia) | 166 | 34 |
| Equal-molar CO$_2$/CH$_4$ mixed-gas permeation (1500 psia) | 71 | 23 |

Both CMS hollow fiber membranes were pyrolyzed without VTMS pre-treatment. While the module assembled with the Duralco™ 4525 epoxy showed consistent CO$_2$/CH$_4$ separation facto at 1500 psia (36 vs 39), the module assembled with the 3M DP-100 epoxy showed much lower separation factor at 1500 psia (23 vs 34). Such results suggest that the 3M DP-100 epoxy may not be suitable for high pressure natural gas permeation of CMS hollow fiber membranes.

The above examples demonstrate a method to make CMS hollow fiber membranes with excellent plasticization resistance for processing high pressure natural gas with high level of condensable CO$_2$. Under 1500 psia equal-molar CO$_2$/CH$_4$ mixed-gas permeation, CMS hollow fiber membranes pyrolyzed from VTMS (25 wt %) pre-treated 6FDA/BPDA-DAM precursor showed attractive CO$_2$ permeance of 93 GPU and CO$_2$/CH$_4$ separation factor of 49. While the example uses CMS hollow fiber membranes derived from 6FDA/BPDA-DAM precursor at the above-specified pyrolysis conditions for natural gas processing, the method can be conveniently extended to CMS membranes formed by other precursor materials under other pyrolysis conditions for a wide range of applications where plasticization or saturation may be a problem.

Figure 4:
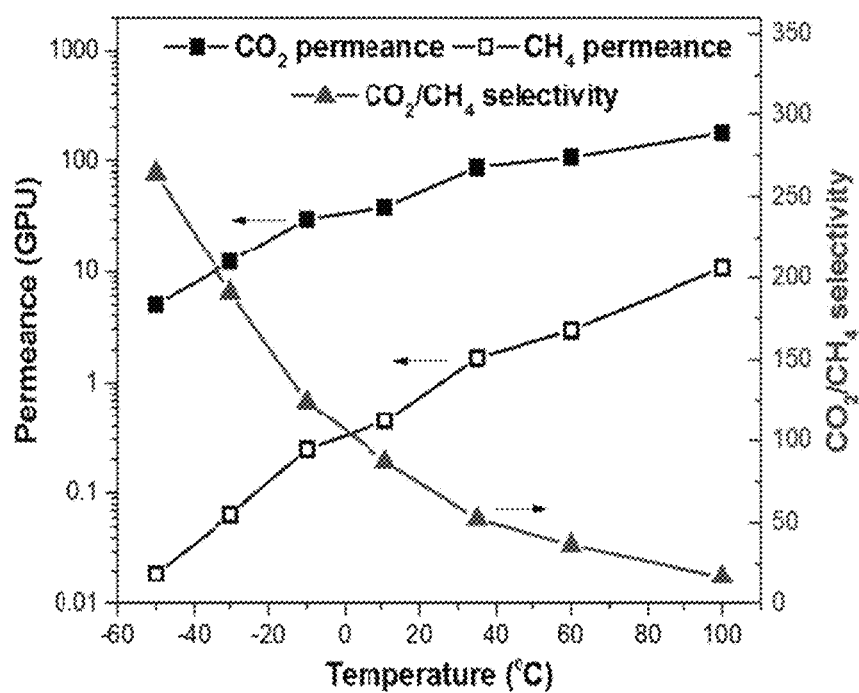
FIG. 4 is an illustration showing the effects of testing temperature on $CO_2$/$CH_4$ mixed-gas permeation data in CMS hollow fiber membranes. Total feed pressure was 800 psia. Feed composition was 50%/50% $CO_2$/$CH_4$ for all temperatures with the exception of −30 and −50° C. (10%/90% $CO_2$/$CH_4$).

Moreover, while the examples use a testing temperature of 35° C., other testing temperatures may be used. It should be noted that transport properties in CMS materials depend on testing temperature. Typically, as testing temperature increases, permeability increases and selectivity drops. FIG. 4 shows an example of the effects of testing temperature on CO$_2$/CH$_4$ mixed-gas permeation data in CMS hollow fiber membranes.

When the presently disclosed CMS membranes are used for the separation of CO$_2$ from natural gas (CH$_4$) having high partial pressures of CO$_2$, the CO$_2$/CH$_4$ selectivity of the CMS membrane may be substantially the same as the CO$_2$/CH$_4$ selectivity of the CMS membrane when subjected to low partial pressures of CO$_2$. For instance, the selectivity of the CMS membrane under high CO$_2$ partial pressure (e.g. at least 20 bar, at least 30 bar, at least 40 bar, at least 50 bar, at least 60 bar, at least 70 bar, or at least 80 bar) may be at least 80%, more desirably at least 85%, more desirably at least 90%, more desirably at least 95% of the selectivity of the CMS membrane under low CO$_2$ partial pressure (e.g. 10 bar or less, about 10 bar, about 9 bar, about 8 bar, about 7 bar, about 6 bar, or about 5 bar). For example, the experimental results in Table 1 demonstrate that the selectivities of the CMS membranes under a CO$_2$ partial pressure of 750 psia (or about 50 bar) are within 90% and 95% of the selectivities of the CMS membrane when subjected to CO$_2$ and CH$_4$ single gas permeation under at 100 psia (or about 7 bar).

Figure 6A:
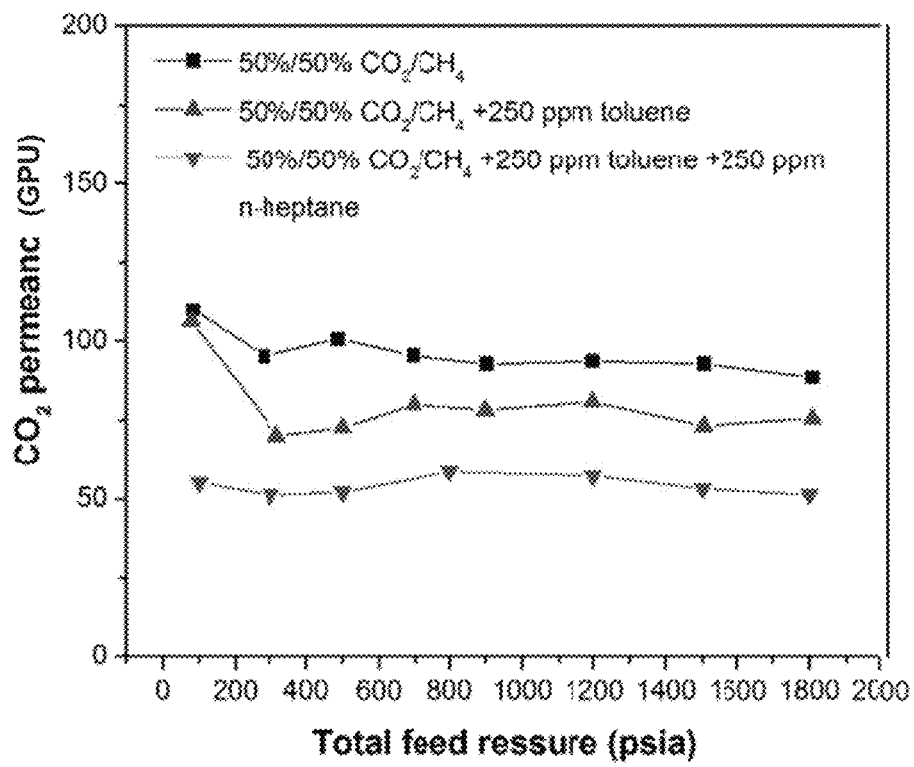
FIG. 6A is a graph showing $CO_2$ permeance data for an embodiment of a CMS hollow fiber membrane prepared in accordance with the present disclosure over a range of feed gas pressures and for feed gases containing varying amounts of hydrocarbon impurities.
Figure 6B:
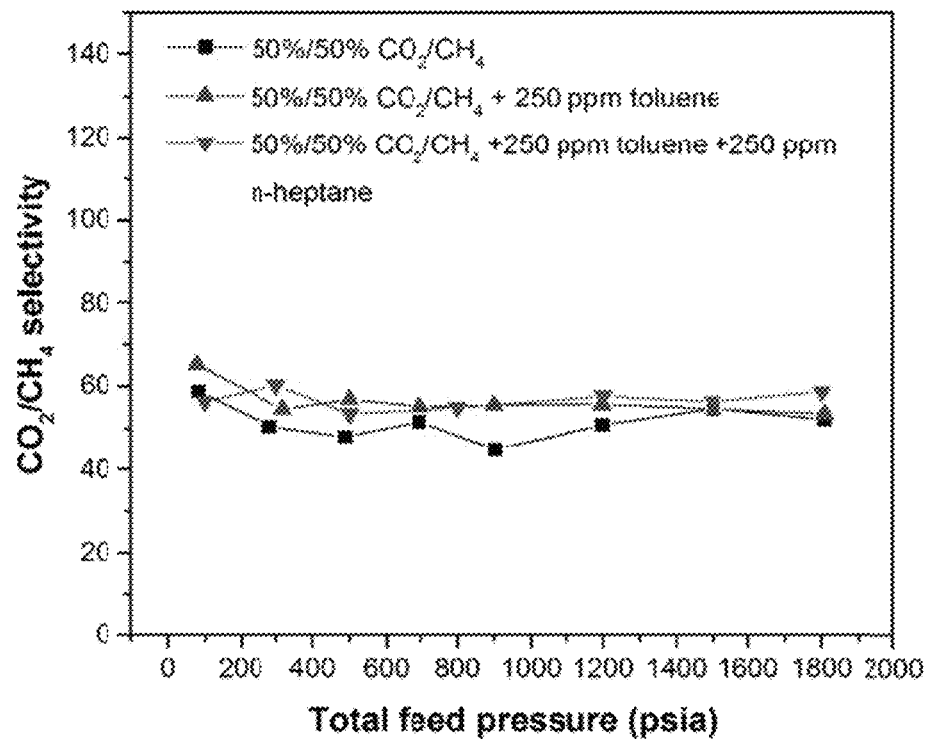
FIG. 6B is a graph showing $CO_2$/$CH_4$ selectivity data for an embodiment of a CMS hollow fiber membrane prepared in accordance with the present disclosure over a range of feed gas pressures and for feed gases containing varying amounts of hydrocarbon impurities.

Additional test data over a range of different pressures is shown in FIGS. 6A and 6B. In this testing, the CO$_2$ peremance and CO$_2$/CH$_4$ selectivity of a carbon molecular sieve membrane prepared in accordance with the present disclosure was subjected to a number of feed gases containing a 50/50 mixture of CO$_2$ and CH$_4$ at pressures between 100 psia and 1800 psia. The testing was performed at 35° C. As shown in FIG. 6B, the CO$_2$/CH$_4$ selectivity of the carbon molecular sieve membrane was substantially unaffected by the high partial pressures of CO$_2$ in the feed gases.

Moreover, the testing was performed using feed gases containing varying amounts of hydrocarbon impurities. Many natural gas sources contain hydrocarbon impurities, such as ethane, propane, butane isomers, pentane isomers, hexane isomers, heptane isomers, benzene, toluene, ethylbenzene, xylene isomers, and combinations thereof. These hydrocarbon impurities are strong plasticizing agents. For example, even at such small amounts as 250 ppm, hydrocarbon impurities such as toluene and n-heptane can cause plasticization and dramatic selectivity loss in uncrosslinked polymer membranes. Nevertheless, as shown in FIG. 6B, the inclusion of toluene and n-heptane impurities in the feed gases had little, if any, effect on the CO$_2$/CH$_4$ selectivity of the carbon molecular sieve membrane across the full range of pressures tested.

Supercritical Separation Processes

Figure 5:
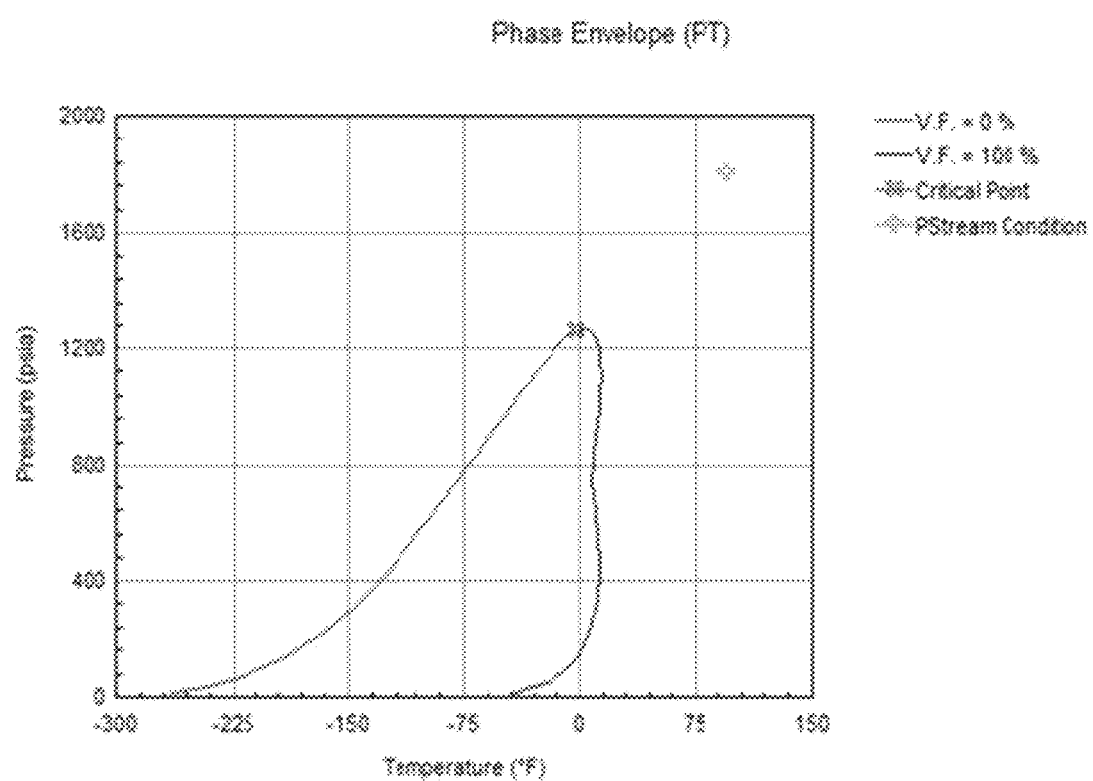
FIG. 5 is an examplary illustration of a phase envelop of 50%/50% $CO_2$/$CH_4$ mixture comprising 250 ppm toluene and 250 ppm heptane. Calculations were done with the Soave-Redlich-Kwong (SRK) model.

A supercritical fluid is any substance at a temperature and pressure above its critical point, where distinct liquid and gas phases do not exist. For example, FIG. 5 shows a critical point of the feed mixture: 50%/50% CO$_2$/CH$_4$ comprising 250 ppm toluene and 250 ppm heptane. The critical point is indicated by the green triangle point.

It has presently been found that carbon molecular sieve membranes may be used to separate supercritical fluids in largely the same manner that it is used to separate gases. In fact, by bringing the feed gas into a supercritical state prior to contacting the feed with a CMS membrane, it has been found that a number of benefits may be achieved.

Separation of gases using carbon molecular sieve membranes traditionally requires a pretreatment of the feed gas in order to prevent the formation of liquids on the membrane surface. The formation of liquids on the membrane surface is a problem because the liquid acts as a resistive layer and therefore decreases the flux through the membrane. Further, the liquid layer is typically composed of condensable components like higher hydrocarbons and water, which can have negative impacts on some membranes. Liquids form on the membrane because (1) the composition of the gas changes from feed to retentate as the sorbed gas(es) is permeated and (2) the temperature changes due to the Joule-Thompson effect as gas travels through in the membrane.

By maintaining the feed and retentate streams at supercritical conditions during the contacting of the feed stream with the membrane, then there is no liquid phase, thus removing the formation of liquids on the membrane surface without requiring a pretreatment.

The feed gas can be brought to a temperature and pressure in the supercritical region by heating, compression, or a combination thereof. Notably, the feed gas should be brought to a point within the supercritical region that ensures that the retentate stream will also be at supercritical conditions, at least in the general vicinity of the membrane. Because the supercritical point of a gas mixture depends on the relative amounts of each gas within that mixture, the supercritical point of the retentate will be different from the supercritical point of the feed due to the sorption of the desired gas component(s). The permeate gas need not be kept at supercritical conditions because the low pressure of the permeate (and at least in the case of $CO_2$ separation from natural gas, the limited amount of hydrocarbons in the permeate) reduce the chance of liquid formation.

Because of the plasticization and saturation effects that would be expected to occur during aggressive gas separations, i.e. gas separations in which the partial pressure(s) of the one or more gas species that are sorbed by the membrane in the feed is/are high, operation at supercritical conditions would be expected to have adverse effects on the ability of the membrane to separate gases. However, based on the surprising findings disclosed herein, membrane separation under supercritical conditions becomes feasible. In fact, at least in the separation of $CO_2$ from natural gas, there seems to be the additional benefit that the high amount of $CO_2$ limits the impact from highly condensing components like toluene, which are known to reduce permeance even when present in very small amounts, as is shown in FIG. 6A.

Various Aspects:

One aspect of the present disclosure is directed to a process for separating at least a first gas component and a second gas component comprising:

a. providing a carbon molecular sieve membrane, such as a carbon molecular sieve membrane prepared by pyrolysis of a rigid, glassy polymer precursor; and b. contacting a gas stream comprising at least a first gas component and a second gas component with the carbon molecular sieve membrane to produce i. a retentate stream having a reduced concentration of the first gas component, and ii. a permeate stream having an increased concentration of the first gas component;

wherein the partial pressure of the first gas component in the gas stream is at least 20 bar, optionally at least 30 bar, optionally at least 40 bar, optionally at least 50 bar, optionally at least 60 bar, optionally at least 70 bar, optionally at least 80 bar, optionally at least 90 bar, and wherein the selectivity of the carbon molecular sieve membrane during the contacting step is at least 80% of the selectivity of the carbon molecular sieve membrane when contacted with a gas stream in which the partial pressure of the first gas component is 10 bar or less under the same conditions, preferably at least 85% of the selectivity of the carbon molecular sieve membrane when contacted with a gas stream in which the partial pressure of the first gas component is 10 bar or less under the same conditions, preferably at least 90% of the selectivity of the carbon molecular sieve membrane when contacted with a gas stream in which the partial pressure of the first gas component is 10 bar or less under the same conditions, preferably at least 95% of the selectivity of the carbon molecular sieve membrane when contacted with a gas stream in which the partial pressure of the first gas component is 10 bar or less under the same conditions.

Another aspect of the present disclosure is directed to a process for separating acid gas components from a natural gas stream comprising:

a. providing a carbon molecular sieve membrane, such as a carbon molecular sieve membrane prepared by pyrolysis of a rigid, glassy polymer precursor; and b. contacting a natural gas stream having a $CO_2$ partial pressure of at least 20 bar, optionally at least 30 bar, optionally at least 40 bar, optionally at least 50 bar, optionally at least 60 bar, optionally at least 70 bar, optionally at least 80 bar, and optionally at least 90 bar, with the carbon molecular sieve membrane to produce i. a retentate stream having a reduced concentration of acid gas components, and ii. a permeate stream having an increased concentration of acid gas components.

wherein the $CO_2/CH_4$ selectivity of the carbon molecular sieve membrane during the contacting step is at least 80% of the $CO_2/CH_4$ selectivity of the carbon molecular sieve membrane when contacted with a gas stream having a $CO_2$ partial pressure of 10 bar or less under the same conditions, preferably at least 85% of the $CO_2/CH_4$ selectivity of the carbon molecular sieve membrane when contacted with a gas stream having a $CO_2$ partial pressure of 10 bar or less under the same conditions, preferably at least 90% of the $CO_2/CH_4$ selectivity of the carbon molecular sieve membrane when contacted with a gas stream having a $CO_2$ partial pressure of 10 bar or less under the same conditions, preferably at least 95% of the $CO_2/CH_4$ selectivity of the carbon molecular sieve membrane when contacted with a gas stream having a $CO_2$ partial pressure of 10 bar or less under the same conditions.

Another aspect of the present disclosure is directed to a process for separating at least a first gas component and a second gas component comprising:

a. providing a carbon molecular sieve membrane, such as a carbon molecular sieve membrane prepared by pyrolysis of a rigid, glassy polymer precursor; and b. contacting a feed stream comprising at least a first component and a second component with the carbon molecular sieve membrane to produce i. a retentate stream having a reduced concentration of the first component, and ii. a permeate stream having an increased concentration of the first component;

wherein the feed stream is at a temperature and pressure in the supercritical region and the retentate stream is at a temperature and pressure in the supercritical region.

It can be seen that the described embodiments provide unique and novel methods for aggressive gas separation that have a number of advantages over those in the art. While there is shown and described herein certain specific structures embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed:

1. A process for separating at least a first gas component and a second gas component comprising:
   a. providing a carbon molecular sieve membrane prepared by pyrolysis of a polymer precursor; and
   b. contacting a gas stream comprising at least a first gas component and a second gas component with the carbon molecular sieve membrane to produce
      i. a retentate stream having a reduced concentration of the first gas component, and
      ii. a permeate stream having an increased concentration of the first gas component;
   wherein the partial pressure of the first gas component in the gas stream is at least 40 bar, and wherein the selectivity of the carbon molecular sieve membrane during the contacting step is at least 80% of the selectivity of the carbon molecular sieve membrane when contacted with a gas stream in which the partial pressure of the first gas component is 10 bar or less under the same conditions.

2. The process of claim 1, wherein the partial pressure of the first gas component in the gas stream is at least 50 bar.

3. The process of claim 1, wherein the first gas component is $CO_2$, $H_2S$, or a mixture thereof and the second gas component is $CH_4$.

4. The process of claim 1, wherein the first gas component is an olefin or a mixture of olefins and the second gas component is a paraffin or a mixture of paraffins.

5. The process of claim 1, wherein the first gas component is $CO_2$ and the second gas component is $N_2$.

6. The process of claim 1, wherein the selectivity of the carbon molecular sieve membrane is at least 90% of the selectivity of the carbon molecular sieve membrane when the partial pressure of the first gas component is 10 bar or less.

7. The process of claim 1, wherein the gas stream and the retentate stream are at supercritical conditions.

8. A process for separating acid gas components from a natural gas stream comprising:
   a. providing a carbon molecular sieve membrane; and
   b. contacting a natural gas stream having a $CO_2$ partial pressure of at least 40 bar with the carbon molecular sieve membrane to produce
      i. a retentate stream having a reduced concentration of acid gas components, and
      ii. a permeate stream having an increased concentration of acid gas components,
   wherein the $CO_2/CH_4$ selectivity of the carbon molecular sieve membrane during the contacting step is at least 80% of the $CO_2/CH_4$ selectivity of the carbon molecular sieve membrane when contacted with a natural gas stream having at a $CO_2$ partial pressure of 10 bar or less under the same conditions.

9. The process of claim 8, wherein the natural gas stream has a $CO_2$ partial pressure of at least 50 bar.

10. The process of claim 8, wherein the $CO_2/CH_4$ selectivity of the carbon molecular sieve membrane during the contacting step is at least 90% of the $CO_2/CH_4$ selectivity of the carbon molecular sieve membrane at a $CO_2$ partial pressure of 10 bar or less.

11. The process of claim 8, wherein contacting a natural gas stream with the carbon molecular sieve membrane occurs at a temperature between −50° C. and 100° C.

12. The process of claim 8, wherein the natural gas stream and the retentate stream are supercritical fluids.

13. A process for separating at least a first gas component and a second gas component comprising:
   a. providing a carbon molecular sieve membrane; and
   b. contacting a feed stream comprising at least a first component and a second component with the carbon molecular sieve membrane to produce
      i. a retentate stream having a reduced concentration of the first component, and
      ii. a permeate stream having an increased concentration of the first component;
   wherein the feed stream is at a temperature and pressure in the supercritical region and the retentate stream is at a temperature and pressure in the supercritical region.

14. The process of claim 13, wherein the first component is $CO_2$, $H_2S$, or a mixture thereof and the second component is $CH_4$.

15. The process of claim 13, wherein the first component is an olefin or a mixture of olefins and the second component is a paraffin or a mixture of paraffins.

16. The process of claim 13, wherein the first component is $CO_2$ and the second component is $N_2$.

* * * * *